United States Patent [19]

Luderschmidt

[11] Patent Number: 5,094,857
[45] Date of Patent: Mar. 10, 1992

[54] TREATMENT OF ACNE OR AND ROGENETIC ALOPECIA BY TOPICAL ADMINISTRATION OF ETHISTERONE

[76] Inventor: Christoph Luderschmidt, Orthstrasse 22, D-8000 Munchen, Fed. Rep. of Germany

[21] Appl. No.: 606,949

[22] Filed: Oct. 31, 1990

Related U.S. Application Data

[63] Continuation of Ser. No. 268,153, Nov. 7, 1988, abandoned.

[30] Foreign Application Priority Data

Nov. 13, 1987 [DE] Fed. Rep. of Germany ....... 3738620

[51] Int. Cl.$^5$ .............................. A61K 7/06; A61K 7/48; A61K 31/565; A61L 15/03
[52] U.S. Cl. ................................ 424/449; 514/859; 514/947; 514/169
[58] Field of Search ................... 514/169–182, 514/859, 947; 424/449

[56] References Cited

U.S. PATENT DOCUMENTS

| | | | |
|---|---|---|---|
| 4,540,564 | 9/1985 | Bodor | 514/176 |
| 4,824,850 | 4/1989 | Bodor | 514/176 |
| 4,829,070 | 5/1989 | Bodor | 514/307 |
| 4,867,982 | 9/1989 | Campbell et al. | 424/449 |
| 4,880,921 | 11/1989 | Bodor | 540/110 |
| 4,895,727 | 1/1990 | Allen | 514/947 |
| 4,900,837 | 2/1990 | Bodor | 546/285 |
| 4,913,905 | 4/1990 | Fankhauser et al. | 424/449 |
| 4,994,278 | 2/1991 | Sablotsky et al. | 424/449 |
| 5,008,257 | 4/1991 | Bodor | 514/192 |
| 5,032,403 | 7/1991 | Sinnreich | 424/449 |

FOREIGN PATENT DOCUMENTS

| | | |
|---|---|---|
| 114003 | 7/1984 | European Pat. Off. . |
| 163489 | 12/1985 | European Pat. Off. . |
| 163490 | 12/1985 | European Pat. Off. . |
| 285563 | 10/1988 | European Pat. Off. . |
| 316780 | 5/1989 | European Pat. Off. . |
| 356382 | 2/1990 | European Pat. Off. . |
| 3338339 | 4/1984 | Fed. Rep. of Germany . |
| 3738620 | 5/1989 | Fed. Rep. of Germany . |
| 3836862 | 5/1990 | Fed. Rep. of Germany . |
| 2131292A | 6/1984 | United Kingdom . |
| 2131292B | 3/1987 | United Kingdom . |

OTHER PUBLICATIONS

Luder Schmidt CA.112:133196w (1989).
Schmidt CA106:149804e (1987).
Mortimer CA.104:136092e(1985).
Mortimer GA.104:136094c (1985).
Luderschmidt GA.104:62161c (1985).
Luderschmidt GA.102:143355e (1984).
Mortimer GA.101:1370455(1984).
Mortimer GA.101:116766n(1984).
Schmidt, J. B. et al., Med. Welt. 36:1122 (1985).
Schmidt, J. B. et al., Hautarzt 38(8):470–473 Aug. (1987).
Toth, F et al., Z. Arztl. Fortbild (Jena) 64(3):122–131 Feb. 1, 1990.
Neumann, F. et al., J. Steroid Biochem. 25(5B):885–895 Nov. 1986.
Schmidt, J. B. et al., Endocrinol Exp. 21(1): 71–78 Mar. 1987.

*Primary Examiner*—Shep K. Rose
*Attorney, Agent, or Firm*—Omri M. Behr

[57] ABSTRACT

There is disclosed the use of ethisterone its nor analogs as well as their corresponding 17-esters formed with pharmaceutically acceptable carboxylic acids, for the reduction of lipids, in particular waxy solids in the sebaceous glands. Such removal facilitates the topical treatment of acne vulgaris or androgenetic alopezia.

7 Claims, 1 Drawing Sheet

TREATMENT OF ACNE OR ANDROGENETIC ALOPECIA BY TOPICAL ADMINISTRATION OF ETHISTERONE

This application is a continuation of application Ser. No. 07/268,153, filed 11/7/88, now abandoned.

FIELD OF THE INVENTION

The invention is directed to the use of certain steroids, notably ethisterone its nor analogs as well as their corresponding 17-esters formed with pharmaceutically acceptable carboxylic acids, for the topical treatment of acne vulgaris or androgenetic alopezia.

DESCRIPTION OF THE PRIOR ART

Acne is a well known inflammatory skin disease of adolescence in which a substantial number of postules are formed in the face. In particularly serious cases the acne may continue over several years, and lead to a permanent scarring of portions of the skin.

Because of the influence of endocrinological action, the sebaceous glands of the skin are stimulated to an over-production of sebum which brings about the saturation of the follicles which with this material, which forms the komedo. This material is formed from numerous components which range from sebaceous residues to keratinous material. The growth of bacteria in these materials and the destruction of the follicles, gives rise to the different symptoms of acne in particular, acne vulgaris.

A substantial number of therapeutic treatment methods of acne have been suggested heretofore which, while they offer a certain measure of relief, do not lead to the cure of this condition. Antibiotics have been applied both topically and systemically to acne patients which had the disadvantage that, because of the buildup of resistance to the applied antibiotics, the treating agent had to be changed after a certain time interval. Furthermore, conventional modes of treatment such as scraping cures, are known wherein layers of skin are removed and thereby the skin channels having occluded sebaceous glands are cleaned. Finally, administration of natural and synthetic hormones was attempted to treat both acne and androgenetically caused loss of hair without achieving a decisive break-through since the side effects i.e. viralization, fertility problems, and the like were to great.

The purpose of the present invention is to provide a material for the treatment of acne and/or androgenetically caused alopezia.

SUMMARY OF THE INVENTION

The solution to the problem lies in the provision of ethisterone, 19-norethisterone and/or the corresponding esters of pharmaceutically acceptable carboxylic acids thereof, or mixtures thereof in a topically acceptable formulation.

It is the surprising finding of this invention that ethisterone which is usually dissolved in an oil-in-water emulsion, when applied to the skin, reduces the total lipid content of the skin by a factor of about 25% from the initial value. It is also noted that there is a reduction of 75% by weight of those lipids which comprise waxy substances which generally have a carbon skeleton of between about $C_{20}$ to about $C_{28}$. By elimination of these waxy substances which are the substantial cause of the closure of the skin pores, the bacteriological degradation which leads to the formation of acne, acne itself can be readily avoided.

It will be understood by those skilled in the art that hereinbelow, the terms ethisterone or nor-ethisterone when utilized alone should be considered to include the 17-esters thereof with pharmaceutically acceptable carboxylic acids suitably lower alkanoic acids containing from 1 to 10 carbon atoms such as formates, acetates, propionates, butyrates, valerates, oenanthates and the corresponding structural isomers thereof.

Ethisterone has been known for thirty years as a gestogenic component which has been widely used as an oral contraceptive. The specific chemical name for ethisterone is 17-alpha-hydroxypregen-4-en-20-yn-3-one (17-alpha-ethynyltestosterone); the nor-analog of ethisterone is known as ethindrone or 17-hyroxy-19-norpregn-4-en-20-yn-3-one (17-alpha-ethynyl-19-nor-testosterone).

This latter material is described for example, in U.S. Pat. Nos. 2,744,122 and 2,949,462. The utilizable esters, in particular, those of the nor-components are described in U.S. Pat. No. 2,964,537. These are formed from the corresponding carboxylic acids having $C_1$ to $C_{10}$ carbon atoms reacting with the 17 hydroxy group. These carboxylic acids are, in particular, those which are listed in U.S. Pat. No. 2,964,537 among these acelic acid is particularly preferred. The disclosures of the foregoing patents are incorporated herein by reference.

DESCRIPTION OF THE PREFERRED EMBODIMENTS

Figure 1:
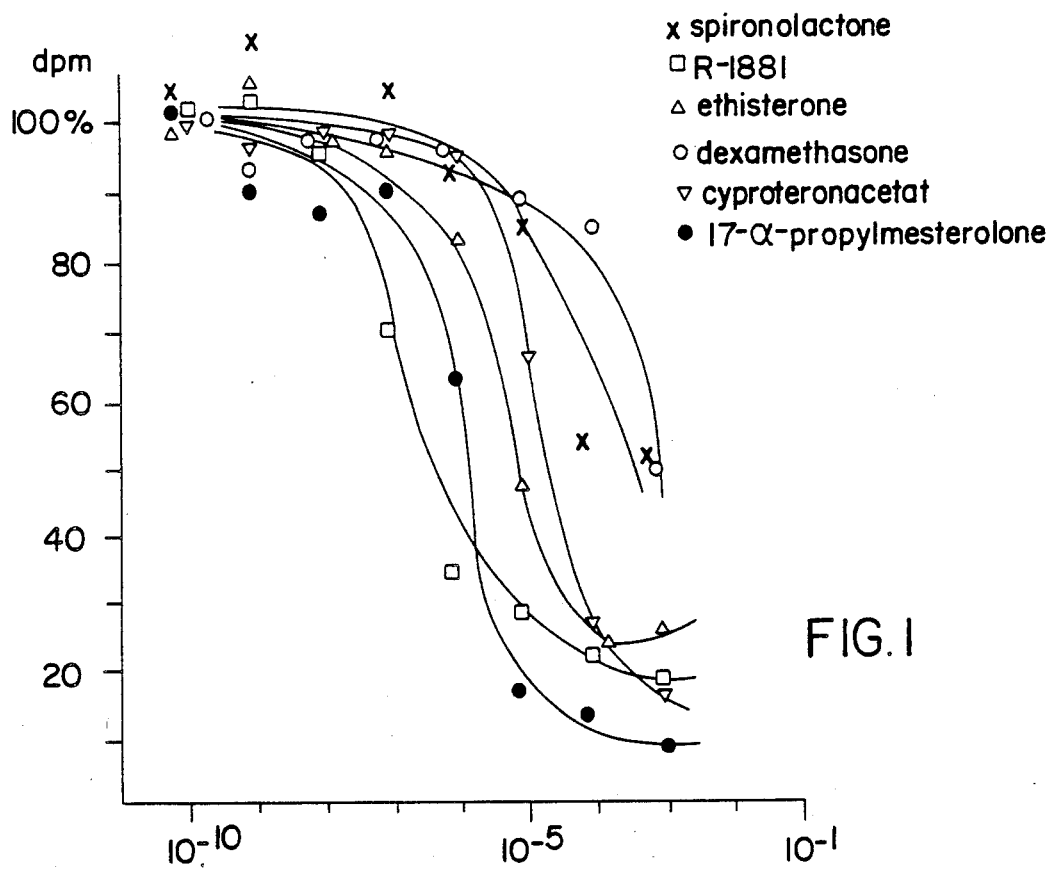

The topical consumption of ethisterone is generally speaking determined by the applied amount rather than the formulation of the applied composition. Hence, the concentration of ethisterone in an transdermal form can be substantially less (i.e. up to a factor of 10) than the conventional oil-in-water emulsions which show substantially no transdermal activity.

It is generally preferred to apply the ethisterone in a concentration of between 0.001 through 1, in particular, 0.01 to 0.1 mg/cm$^2$ of skin surface area, the latter amount is the one which should reach the receptor position. The composition is generally applied one to three times daily in the usual amounts whereby under usual amounts those amounts are understood which will lead to the formation of a thin film on the treated skin. The treatment is continued so long as necessary until the symptoms of the disease disappear. Ethisterone can be dissolved in the usual topical formulations and applied to the skin surface in question in such formulations for example, creams, lotions, solutions, sprays and the like.

Among applicable transdermal systems there may be utilized alcoholic solution systems, which usually comprise ethanol or propanol. The solubility of the ethisterone in alcoholic systems can be improved, by the provision thereto of surfactant materials such as polyethylene glycols. Especially suitable as polyethylene glycols are those sold in commerce under the Trademark of "Tween" 20-80. Similarly surface active agents such as sorbitan esters may be utilized which are known in commerce under the Trademarks of "Tegan" or "Span".

As liquid formulation there may similarly be used alcohols, in particular, ethanol, isopropanol; acetone; glycerine; glycols, such as propylene glycol; mineral oils, aqueous cellulose containing derivatives as well as liquid fluorinated hydrocarbons (freons) of these components ethanol or isopropanol is preferred.

In order to improve the action of these alcohols a lipophilic surface active agent is usually added for example, a modified polyethylene glycol. In such a mixture there is utilized a ratio of 30:70 to 70:30, of these components relevant to 100 parts by weight.

In addition to these systems there may also be utilized creams for example, cold cream as formulated in the U.S. Pharmacopoea.

Generally speaking, such formulations contain between 0.5 and 2 suitably 1% by weight of ethisterone. Depending upon the dispersability of ethisterone in these materials, these concentrations may be raised or lowered.

The concept of the present invention is not limited to the use of ethisterone for the treatment of acne, but may also be directed to the relief of androgenetic alopezia which causes the genetically determined loss of hair which loss increases with age and leads eventually, in many cases, to total baldness. A further material for the combatting androgenic alopezia is 17-alpha-propyl-mesterolone (17-a-PM) which is sold by Schering AG.

It is believed that androgenetic alopezia is caused by the hypersensitization of certain receptors impacted by hormones which eventually leads to the loss of hair. It is the surprising finding of the present invention that the aforementioned substances in particular, ethisterone and propyl mesterolone competitively block the binding sites and so relieve the hypersensitization so as to permit the growth of hair on the portions affected by alopezia.

The therapeutically effective amounts are similar to those listed above in the treatment of acne. The same formulations utilized for the treatment of acne may, similarly be utilized in these circumstances.

EXAMPLES

Example I

For the treatment of acne the following material may be utilized:

1% by weight preparation of ethisterone in an oil and water emulsion, sold under the Trademark "PHYSIANE" sold by Roche-Posay. Physiane comprises polyoxyethyl gylceride, 0.5% parceol, 1% glycerine and oleic acid.

In accordance with the above formulation, in place of ethisterone, there may be employed nor-ethisterone, the acetates or valerates of ethisterone or norethisterone, or 17-alpha PM.

Example II

For the treatment of androgenetic alopezia the following composition may be utilized:

2% nor-ethisterone in a mixture of 50% by weight of ethanol and 50% by weight of "Tween" 20.

Example III

In place of nor-ethisterone set forth in Example II, there may be utilized 17-alpha-propylmesterolone.

Example VI

Hair Growth Material.

A 2% solution of nor-ethisterone in 50% ethanol and 50% Tween 20, was utilized for the assistance in hair growth by androgenetic alopezia. The bald spots were rubbed twice daily with a sufficient amount of hair growth material to provide a concentration of 1 mg per $cm^2$ nor-ethisterone through the skin barrier to the receptor site. After only four weeks, a hair fuzz is noted on the previously bald spot. When ethisterone is replaced in this example by 17-Propylmesterelone practically the same result is obtained because of the very small amounts of hormones utilized and absorbed into the organism, no undesirable side effects were noted.

TEST EXPERIMENTS

The Syrian hamster is especially suitable as in vivo test animals because of the very voluminous subaceous glands in its ventral ear shell sides. These glands are very similar in anatomical structure (phylo-sebo glandular entity) to human sebaceous glands, are believe to apply a homostatic drive mechanism to the androgen dependent sebum synthesis.

The presence of high concentrations of androgen receptors may be demonstrated in the animal sebaceous glands by the use of dextran coated activated charcoal absorption. This receptor activity can itself be controlled by androgens.

The affinity of synthetic steroids such as ethisterone, ethindrone, 17-alpha PM, cyperone acetate (CPA) and spironolactone (SL), are determined by competitive binding analysis.

The standardisation basis in competitive binding analysis is the concentration of the competitor which, can displace 50% of a radioactively labeled reference substance from the receptor. This is conditioned upon the assumption that a relative binding efficiency (RPA) is proof of a high receptor quantity in the test material.

In the following experiments the relative affinity of 17-alpha PM, CPA, SL, R1881, ethisterone and dexamethasone where determined with respect to the androgen receptor preparations of sebaceous glands of Syrian hamsters. The comparison of the in vivo sebum suppression with RBA to the androgen receptor in vitro, should give the key to the answer of whether the substance itself or metabolites thereof, are responsible for the activity.

ANIMAL MODEL

Sexually mature male Syrian hamsters (110 to 120 grams) were utilized. The animals were exposed to light for 14 hours per day. They were kept in individual cages, and were fed commercial food as well as water ad libitum. As previously mentioned, 17-alpha PM, CPA, SL, ethisterone, dexamethasone, and R1881 (methyltrienolone) were utilized as test substances.

DCC ASSAY

The receptor quality and quantity were determined by means of the DCC assay. See {Luderschmidt et al., Focus on Acne Vulgaris (Ed. Collen, 1985, p. 131 to 140, Roy. Soc. Med Serv., London, 1985) and Nissen and Luderschmidt "Fats, Soaps and Coating Materials" (1985) p. 567 to 570. published by . . . }

Cytostolic supernate, for the proof of androgen receptor activity with rising concentration, was incubated with R 1881 (0.5, 1, 2, 4,8 nM.)

The non-specific binding was achieved by treating parallel amounts of cytostol with an excess of unlabeled R 1881 and triamcinolone (4.000 nM). Equilibrium was reached during a incubation time of 12 hours at 4° C. The free, unbound steroid was removed with dextran coated activated charcoal in buffer B (0.5% activated charcoal, 0.5% dextran, 10 m Mol/l, Tris-HCl, pH 7.4).

The radioactivity in the supernate corresponded to the total of the non-specific binding.

COMPETITIVE BINDING ANALYSIS

For the competitive study the web material of five ear shells was gathered. After homogenization in buffer A (10 mM-Tris-HCl-pH 7.4; 1.5 mM EDTA; 5 mM monothiogylcerine) cytosol was obtained as a supernate after ultracentrification at $120 \times 10^3$ g for thirty minutes at 4° C. The protein content was adjusted to between 1 to 5 mg/ml with a buffer A.

For the experimental series for the determination of the affinity of a ligand to an androgen receptor, rising concentrations ($10^{-3}$ to $10^{-10}$ mole) were incubated with a constant concentration (8 nM) of tritium marked R 1881 (specific activity 87 Ci/mm, NEN NET 590). Since the synthetic steroid R 1881 binds both to the gestagen and the glucocorticoid receptors, all of the reaction samples were additionally incubated with an excess of triamcinolone acetate (4000 nM).

After a reaction time of 12 hours at 4° C. to achieve equilibrium, the unbound steroid hormones were removed from the reaction mixture by means of dextran-coated activated charcoal suspension (0.5% activated charcoal and 0.05% detran in 10 nM Tris-HCl-buffer; pH 7.4). An aliquot of the supernate after centrifugation was measured in a fluid scintillation counter. The results obtained for concentrations of $10^{-3}$ to $10^{-5}$M of a substance, which correspond to the displacement of tritium-marked R 1881 from the adrogenreceptor, were evaluated with the so called Scatchard-plot and previously applied saturation analysis.

RESULTS

DCC ASSAY: Androgen receptors of high freebinding capacity may be shown in the subaceous glands of Syrian hamsters. The concentrations vary between 88 and 425 fmol/mg cytosolic protein with a mean value of $233 +/- 154$ fmol/mg cytosolic protein. The dissociation constants of the tritium-marked R 1881 androgen receptor complexes are at a level of $2.92 +/- 0.64 \times 10^{-9}$ and correspond to a specific binding. By means of a saccharose-density gradient centrifugation the androgen receptors are characterized as belonging to the 8S-fraction.

COMPETITIVE BINDING ANALYSIS

The result of the displacement exponents of the tritum-market R 1881 marked androgen receptors for the above-identified substances are shown in FIG. 1.

From this the in vitro affinity at 50% blocking may be set forth in the following order: R 1881, 17-alpha-PM, ethisterone, CPA, SL and dexamethasone.

Herein 17-alpha-PM shows a substantially higher affinity for the androgen receptors. On the other hand the RBA of synthetic dexamethasone may be disregarded as an androgen receptor in realistic concentrations. Furthermore, it may be deduced that ethisterone takes a satisfactory middle place between 17-alpha-PM and synthetic R 1881.

Figure 2:
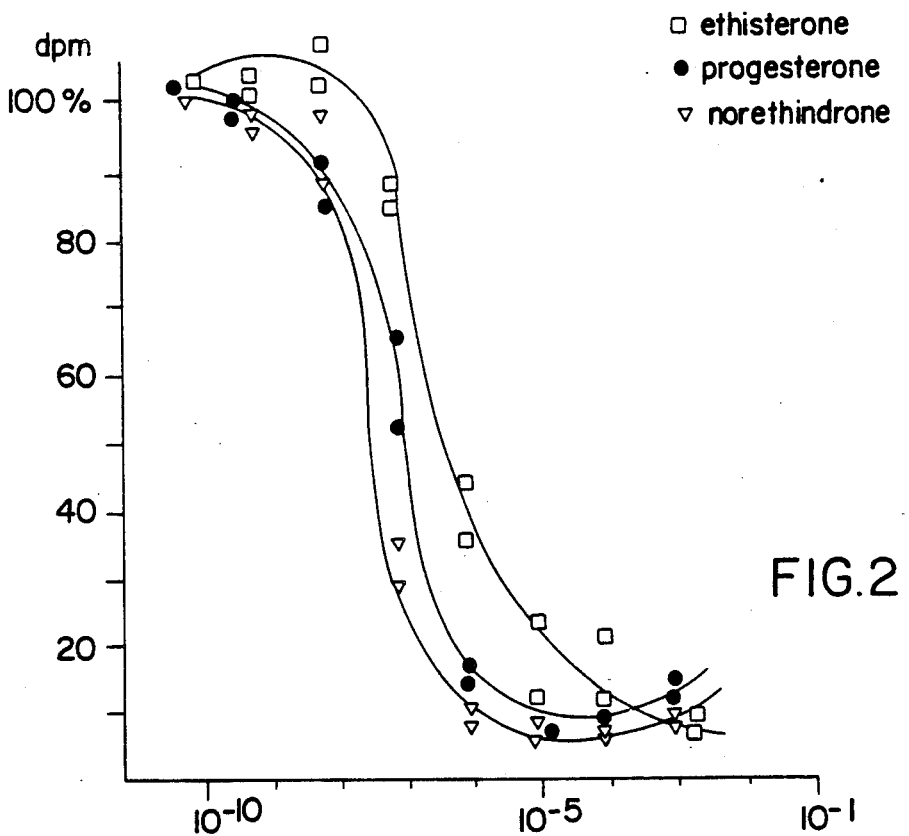

FIG. 2 shows the binding relationship to gestogen receptors in a sheep uterus of ethisterone, nor-esthisterone and progesterone whereby nor-ethisterone has a higher binding affinity than progesterone and ethisterone. These experiments relating to the competitive binding of different hormanal substances can only describe certain aspects of the binding kinetics, but not all aspects of the pharmacokinetics. It is thus necessary to test the biological effects of steroid hormones by in vivo methods.

HUMAN STUDIES

A 2% ethisterone formulation was prepared in accordance with Example I. Five male and five female human test subjects took part in the experiment who were treated on their left foreheads with the ethisterone lotion. The subjects applied the lotion twice a day at a concentration of approximately 0.1 mg per cm$^2$ of ethisterone applied to the receptors.

The lipid content of the upper skin surface of both left and right forehead portions were measured prior to the onset of therepy (0 control), in the second and the fourth weeks of therapy.

Initially the replacement sum was determined. The skin was first cleaned with cigarette paper dipped in acetone and stroked six to eight times over the test area. After sixty minutes the skin lipids were removed from the skin portion of the following manner. Cigarette paper was placed by means of tweezers on the segment to be measured and on the cigarette paper was placed a mass of 280 grams having a surface area of 5 cm$^2$. Thereafter, the paper was eluted with a mixture comprising 70 parts of acetone and 30 parts of methanol. The thus produced eluate was evaporated to dryness and treated with phosphovanillic acid, thereafter the eluate was evaluated by gas chromatography. Previously, the gas chromatograph had been calibrated with 25 standard skin lipids (mono-di-, triglyceride, cholesterol as well as cholesterol esters, oleic acid esters, having 10 to 18 carbon atoms as well as waxes having up to 28 carbon atoms).

The eluate was also subjected, to thin layer chromomatography. It is noted that generally, speaking the standard substances may be regarded as representative of skin upper surface lipids.

After a four week treatment with the above-identified lotion it could be determined that the lipid content on the treated skin upper surface area was 25% less then the lipid content of the untreated area. It is interesting to note that the wax content however, was reduced by 75% which removes the basis for the formation of acne.

I claim:

1. A method of treating androgenetic diseases of the skin by trandermally administering to the skin surface to a subject in need of such treatment, a concentration of 0.01 to 1 mg./cm$^2$ of skin surface of at least one member of the group of steroids consisting of ethisterone, norethisterone and the 17-esters thereof derived from pharmaceutically acceptable carboxylic acids.

2. A method of treating acne by transdermally administering to the skin surface to a subject in need of such treatment, a concentration of 0.01 to 1 mg./cm$^2$ of skin surface of at least one member of the group og steroids consisting of ethisterone, norethisterone and the 17-esters thereof derived from pharmaceutically acceptable carboxylic acids.

3. A method of treating androgenetically caused alopecia by transdermally administering to the skin surface so as to permit the growth of hair on the portions affected by alopecia, of a subject in need of such treatment, a concentration of 0.01 to 1 mg./cm$^2$ of skin surface of at least one member of the group of steroids consisting of ethisterone, norethisterone and the 17-esters thereof derived from pharmaceutically acceptable carboxylic acids.

4. A method of claim 1 wherein the steroids are applied at a concentration of 0.01 to 0.1 mg/cm² of skin surface.

5. A method of claim 1 wherein the steroids are applied in a thin film between 1 and 3 times daily.

6. A method of claim 1 wherein the steroids are dissolved or suspended in a transdermal carrier pharmacologically compatible with skin.

7. A method of claim 6 wherein the carrier is a cream, lotion, ointment, solution or spray.

* * * * *